United States Patent

(12) United States Patent
Zeika et al.

(10) Patent No.: US 12,221,437 B2
(45) Date of Patent: Feb. 11, 2025

(54) BISPYRANILIDENES, DITHIOBISPYRANILIDENES AND DISELENOBISPYRANILIDENE AND USE THEREOF

(71) Applicant: SENORICS GMBH, Dresden (DE)

(72) Inventors: Olaf Zeika, Meißen (DE); Christina Kaiser, Swansea (GB); Koen Vandewal, Overpelt (BE); Bernhard Siegmund, Dresden (DE); Johannes Benduhn, Dresden (DE); Manuel Tropiano, Dresden (DE)

(73) Assignee: SENORICS GMBH, Dresden (DE)

( * ) Notice: Subject to any disclaimer, the term of this patent is extended or adjusted under 35 U.S.C. 154(b) by 676 days.

(21) Appl. No.: 17/595,735

(22) PCT Filed: May 14, 2020

(86) PCT No.: PCT/EP2020/063434
§ 371 (c)(1),
(2) Date: Nov. 23, 2021

(87) PCT Pub. No.: WO2020/239456
PCT Pub. Date: Dec. 3, 2020

(65) Prior Publication Data
US 2022/0135549 A1 May 5, 2022

(30) Foreign Application Priority Data
May 29, 2019 (DE) ...................... 10 2019 114 456.6

(51) Int. Cl.
C07D 409/14 (2006.01)
C07D 495/04 (2006.01)
H10K 30/30 (2023.01)
H10K 85/60 (2023.01)
H01G 9/20 (2006.01)

(52) U.S. Cl.
CPC ......... C07D 409/14 (2013.01); C07D 495/04 (2013.01); H10K 85/653 (2023.02); H10K 85/655 (2023.02); H10K 85/657 (2023.02); H01G 9/2059 (2013.01); H10K 30/30 (2023.02)

(58) Field of Classification Search
CPC .. C07D 409/14; C07D 495/04; H10K 85/655; H10K 85/657; H10K 85/653; H10K 30/30; H01G 9/2059
See application file for complete search history.

(56) References Cited

U.S. PATENT DOCUMENTS

2011/0083730 A1 4/2011 Fichou et al.
2018/0198005 A1 7/2018 Siegmund et al.

FOREIGN PATENT DOCUMENTS

| DE | 102015101768 A1 | 8/2016 |
|---|---|---|
| EP | 3152785 B1 | 4/2017 |
| JP | 2005-035980 A | 2/2005 |
| JP | 2016-503581 A | 2/2016 |

OTHER PUBLICATIONS

Mabon et al., 13(8-9) New Journal of Chemistry, 601-7 (1989) (Year: 1989).*
Mabon et al., "The Cathodic Coupling of Heterocyclic Activated Thioketones. A New and Efficient Route to π-Donors (I)—The Synthesis of Polysubstituted Bipyranylidenes From 4H-Pyran 4-Thiones", New J. Chem., 1989, 13, 601-607.
International Search Report (and English translation) and Written Opinion of the International Searching Authority for International Application No. PCT/EP2020/063434 mailed on Jul. 1, 2020.
Kaiser et al., Chemistry of Materials., "Manipulating the Charge Transfer Absorption for Narrowband Light Detection in the Near-Infrared", 2019, 31, 9325-9330.
Bolag et al., "Field-Effect Transistors Based on Tetraphenyldipyranylidenes and the Sulfur Analogues," Chem. Mater., 2009, 21, 4350-4352.

* cited by examiner

Primary Examiner — Timothy R Rozof
(74) Attorney, Agent, or Firm — HESLIN ROTHENBERG FARLEY & MESITI P.C.

(57) ABSTRACT

The invention relates to bispyranilidenes, dithiobispyranilidenes and diselenobispyranilidene according to formula (I), to the use thereof as light or IR-absorber and to an electronic or optoelectronic component containing at least one compound according to formula (I).

20 Claims, 3 Drawing Sheets

Figure 1:
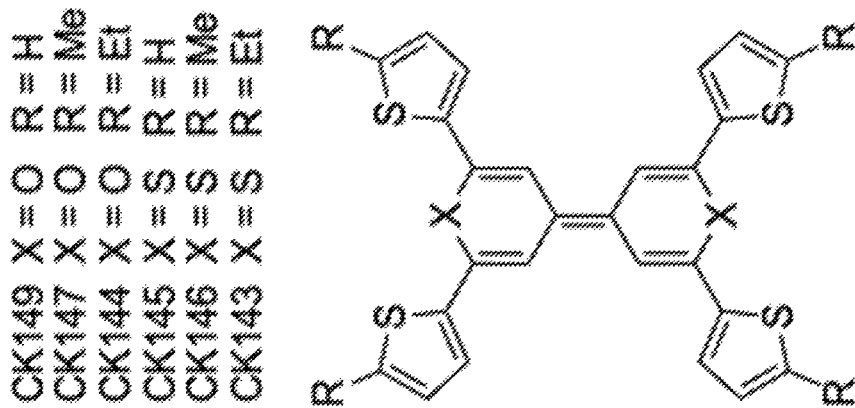
Figure 1:
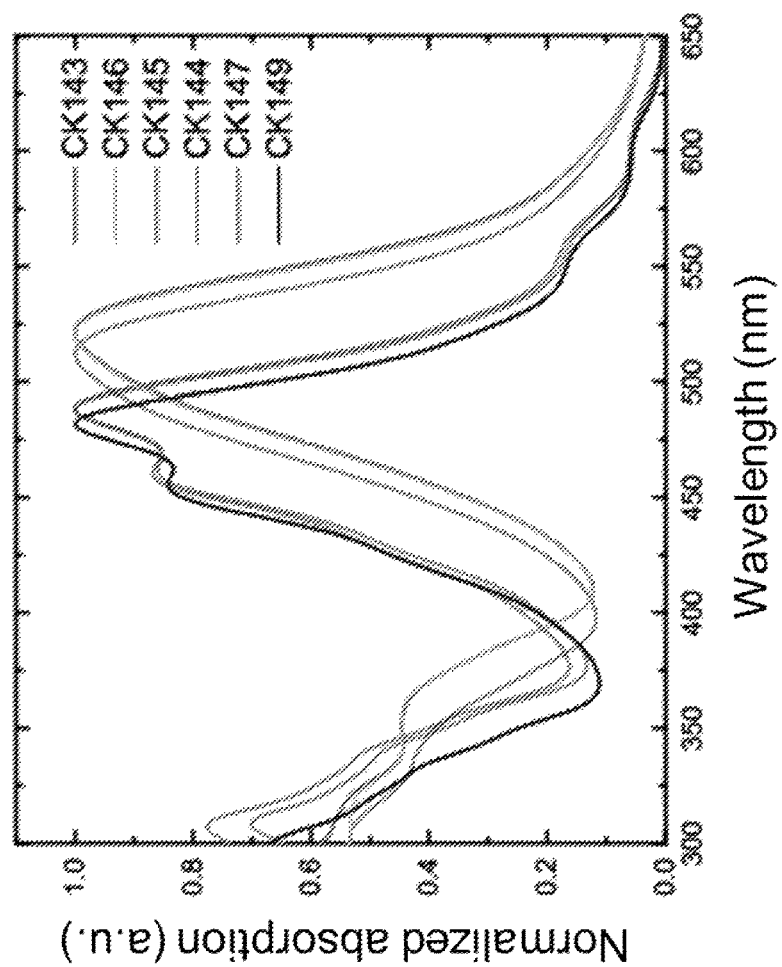

BISPYRANILIDENES, DITHIOBISPYRANILIDENES AND DISELENOBISPYRANILIDENE AND USE THEREOF

CROSS REFERENCE TO RELATED APPLICATIONS

This application is a national stage filing under section 371 of International Application No. PCT/EP2020/063434 filed on May 14, 2020, and published on Dec. 3, 2020 as WO 2020/239456, which claims priority to German Application No. 10 2019 114 456.6, filed on May 29, 2019. The entire contents of WO 2020/239456 are hereby incorporated herein by reference.

The invention relates to bispyranilidenes, dithiobispyranilidenes and diselenobispyranilidenes according to formula (I), to the use thereof as light or IR-absorber and to an electronic or optoelectronic component containing at least one compound according to formula (I).

Optoelectronic components possess the ability to either convert light, in particular sunlight, into electricity or vice versa. This class of devices includes solar cells, OLEDs, and sensors, especially photodetectors. Solar cells are optimized to convert as much of the sunlight as possible into electrical power. Detectors, on the other hand, are often operated with an externally applied voltage to achieve higher external quantum efficiencies in the detection range and faster response times. The detection range can be in visible and outside visible light.

Electronic components, such as organic field-effect transistors (OFETs), can consist of a very thin insulator film and an organic semiconductor layer in addition to the three contacts (source, drain, gate), whose drain voltage/current characteristics depend significantly on the gate voltage.

The development of compounds for use in electronic and optoelectronic components is currently the subject of intensive research. The aim is to develop and investigate compounds that enable an improved property profile, especially in terms of absorption ranges, electrical mobility and thus device efficiencies.

Strzelecka et al. disclose the study of optical and electrical properties of unsubstituted dipyranylidenes and dithiopyranylidenes substituted by a methyl group, aryl group, or thiophene group (Strzelecka et al. 1979). The compounds are used to prepare TCNQ molecular complexes. Fabre et al. disclose dipyranylidenes substituted with various aromatic residues, especially with phenyl, p-tolyl or thiophene groups (Fabre et al. 1976).

Mabon et al. describe a process for the preparation of various tetrasubstituted dipyranylidenes, in particular symmetrical and unsymmetrical dipyranylidenes, substituted with methyl or aryl groups, such as phenyl, thiophene or anisyl groups (Mabon et al. 1989).

One variant for improving the property profiles of optoelectronic devices, such as photovoltaic cells and photodetectors, especially near-infrared (NIR) and infrared (IR) sensors, is the use of so-called charge-transfer transitions. Charge transfer transitions (CT) are divided into intermolecular and intramolecular charge transfer transitions. A charge transfer transition is a complete or nearly complete charge transfer from a donor compound to an acceptor compound. If both compounds are anchored in the same molecule, an intramolecular charge transfer transition is present. If different (discrete) molecules or ions, which may also be loosely coupled by coordinative interaction, act as donor compound and acceptor compound, this is called intermolecular charge transfer. The intermolecular charge transfer transition typically leads to electrostatically bound donor-acceptor complexes.

An intermolecular charge transfer state is a weakly bound state between an excited electron in the LUMO (or higher energy state) and a hole in the HOMO (or lower energy state), said hole and electron being on spatially separated molecules. Preferably, the charge transfer state is formed at the interface between the donor compound and the acceptor compound. Subsequently, the donor compound, excited as a result of absorption of electromagnetic radiation, transfers the negative charge from the LUMO to the LUMO of the acceptor compound via interchromophoric charge transfer or enters the ground state by recombination.

EP 3 152 785 B1 and Siegmund et al. describe near-infrared photodetectors based on intermolecular charge-transfer absorption (Siegmund et al. 2017), in particular the use of optical microcavities to increase more than 40-fold the typically negligible external quantum efficiency (EQE) in the spectral range of charge-transfer absorption. Siegmund et al. describe EQEs above 20% as well as spectral linewidths down to 36 nm and resonance wavelengths between 810 nm and 1550 nm based on blends of $C_{60}$ fullerene and donor materials with high HOMO levels, in particular $ZnPc:C_{60}$ and $TPDP:C_{60}$.

EP 3 152 785 B1 describes the detection of an electromagnetic signal in the spectral wavelength range from 780 nm to 10 μm using donor compounds preferably selected from the substance group of phthalocyanines, such as zinc phthalocyanine or iron phthalocyanine; of pyrans, such as bispyranilidenes, in particular TPDP; the fulvalenes, such as tetrathiofulvalene, or the aromatic amines, such as N,N,N',N'-tetrakis(4-methoxyphenyl)-benzidines, 2,7-bis[N,N-bis(4-methoxy-phenyl)amino]9,9-spiro-bifluorenes or 4,4',4''-tris(3-methylphenyl-phenylamino)triphenylamine), the bisthiopyranilidenes, the bipyridinylidenes or the diketopyrrolopyrroles and an acceptor compound preferably selected from fullerenes, such as $C_{60}$.

Bolag et al. disclose field-effect transistors based on tetraphenyldipyranilidenes (TPDP) and their sulfur analogs (Bolag et al. 2009). Bolag et al. describe the stability of the cations and dications of tetraphenyldipyranilidenes, the extended π-system, which is advantageous for intermolecular interactions, a simple fabrication procedure, and high absorption in the visible region. Furthermore, Bolag et al. reveal higher performance of the sulfur compound over tetraphenyldipyranilidenes due to higher crystallinity, and the introduction of halogen substituents to increase stability and solubility.

DE 10 2015 101 768 A1 discloses unsubstituted and substituted quinoid aromatics, polyaromatics, heteroaromatics or polyheteroaromatics, their possible use in an optoelectronic component, as well as the optoelectronic component and its use as an IR absorber in films and thin films, in particular in heat insulating glazings.

US 2011/0 083 730 A1 discloses symmetrical and unsymmetrical compounds of the formula (I)

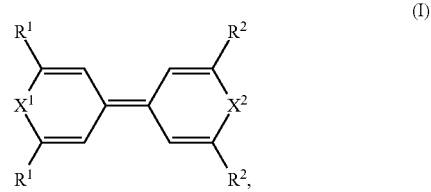

where $X^1$ and $X^2$ are independently selected from N, P, O, S, Se and Te, and $R^1$ and $R^2$ are independently selected from unsubstituted or substituted aromatics and heteroaromatics having from 4 to 10 carbon atoms, as well as their use in electronic and optoelectronic devices. Thiophenyl and alkoxythiophenyl residues, in particular

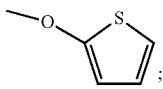

furyl, pyrrolyl, pyridyl, pyrazyl, pyrazolyl, pyridazyl, pyrimidyl, triazyl, imidazolyl, oxazolyl, indyl, indazolyl, quinolyl and quinoxalyl residues are disclosed as heteroaromatics.

Despite the improved efficiencies for optoelectronic components achieved by various approaches, the efficiencies and component lifetimes currently achieved are not yet sufficient for commercial use.

Therefore, it is the object of the present invention to provide organic photoactive compounds that exhibit high absorption intensity.

Furthermore, it is an object of the invention to provide electronic or optoelectronic components with high efficiencies.

According to the invention, the task is solved by a compound according to formula (I)

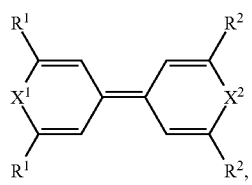

(I)

wherein $X^1$ and $X^2$ are each independently selected from the group comprising oxygen, sulfur, and selenium, wherein $R^1$ and $R^2$ are each independently selected from the group comprising substituted thiophene and selenophene residues.

Advantageously, the compounds according to the invention show high thermal stability. Advantageously, the compounds according to the invention can be sublimed under high vacuum. Further advantageously, the compounds according to the invention exhibit photoactivity in the visible and infrared range. Advantageously, the compounds according to the invention are electron donor compounds and particularly advantageously, the compounds according to the invention exhibit long wavelength and intense absorbing charge transfer (CT, charge transfer) transitions with suitable p-acceptor materials. The reason for the shift of the absorption of the compounds according to the invention with substituted thiophene and selenophene residues beyond the CT state into the further red or longer wavelength absorption region is due to the broadening and enhancement of the HOMO state, which increases the overlap with the LUMO energies and thus also the overlap with the acceptor used.

In further embodiments, $R^1$ and $R^2$ are each independently selected from the group comprising

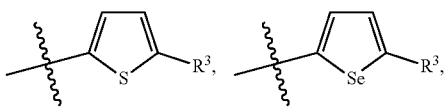

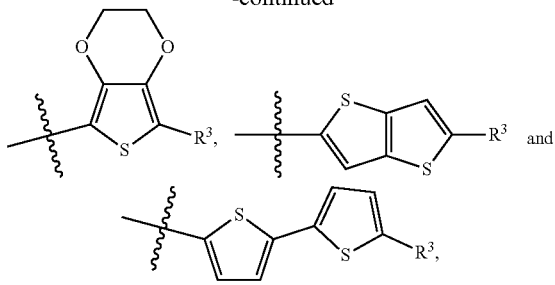

wherein $R^3$ is selected from C1 to C20 alkyl and cycloalkyl residues, C1 to C20 perfluoroalkyl residues, C1 to C20 aryl and heteroaryl residues, C1 to C20 alkoxy and thiaalkoxy residues, and primary, secondary, and tertiary C1 to C20 alkylamino residues.

"Perfluoroalkyl residues" are alkyl residues in which all hydrogen atoms are replaced by fluorine atoms. Preferred perfluoroalkyl residues are selected from the group comprising trifluoromethyl, pentafluoroethyl, heptafluoropropyl, iso-heptafluoropropyl, nonafluorobutyl, tert-nonafluorobutyl and iso-nonafluorobutyl.

The term "primary alkylamine residues" refers to derivatives of ammonia in which one hydrogen atom is replaced by an alkyl residue, such as methylamine.

The term "secondary alkylamine residues" refers to derivatives of ammonia in which two hydrogen atoms are each replaced by an alkyl residue, such as dimethylamine or ethylmethylamine.

The term "tertiary alkylamine residues" refers to derivatives of ammonia in which three hydrogen atoms are each replaced by an alkyl residue, such as trimethylamine or ethyldimethylamine.

In further embodiments, primary, secondary, and tertiary C1 to C20 alkylamine residues comprise cyclic amines, in particular cyclic secondary amines, and bistolylamines.

In further embodiments, $R^3$ is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclobutyl, cyclopentyl, cyclohexyl, cycloheptyl, trifluoromethyl, pentafluoroethyl, heptafluoropropyl, iso-heptafluoropropyl, nonafluorobutyl, tert-nonafluorobutyl, iso-nonafluorobutyl, 2,2,2-trifluoroethyl, 2,2,3,3,3-pentafluoropropyl, 2,2,3,3,4,4,4-heptafluorobutyl, 2,2,3,3,4,4,5,5-nonafluoropentyl, 2,2,3,4,4,5,5,6,6-unododecafluorohexyl, phenyl, benzyl, diphenyl, naphthyl, anthryl, phenanthryl, pyridyl, furanyl, thienyl, thiazyl, oxazyl, imidazyl, pyrimidyl, thiazinyl, methoxy, ethoxy, propoxy, butoxy, pentoxy, thiomethoxy, thioethoxy, thiopropoxy, iso-thiopropoxy, thiobutoxy, iso-thiobutoxy, tert-thiobutoxy, thiohexoxy, iso-thiohexoxy, amino, methylamino, butylamino, tolylamino, dimethylamino, diethylamino, methylphenylamino, methyltolylamino, pyrrolidine, piperidine, morpholine, thiomorpholine and ditolylamine.

In a preferred embodiment, $R^3$ is selected from the group consisting of unsubstituted and substituted C1 to C20 alkyl residues, particularly preferably from the group consisting of methyl, ethyl, propyl, butyl, pentyl and hexyl.

In one embodiment, $R^1$ und $R^2$ are identical.

In further embodiments, $X^1$ and $X^2$ are oxygen and sulfur, oxygen and selenium, or sulfur and selenium.

In preferred embodiments, $X^1$ and $X^2$ are each independently selected from the group comprising sulfur and selenium.

In a preferred embodiment, $X^1$ and $X^2$ are identical. In a preferred embodiment, $X^1$ and $X^2$ are selected from the group comprising oxygen, sulfur, and selenium, and $X^1$ and $X^2$ are particularly preferably sulfur.

In further embodiments, the compounds according to the invention are symmetrical, wherein $R^1$ and $R^2$ and $X^1$ and $X^2$ are identical.

Particularly preferred embodiments of the compounds according to the invention are the following individual compounds:

2,2',6,6'-Tetra-(2-methylthienyl)-4,4'-bispyranilidene,
2,2',6,6'-Tetra-(2-ethylthienyl)-4,4'-bispyranilidene,
2,2',6,6'-Tetra-(2-propylthienyl)-4,4'-bispyranilidene,
2,2',6,6'-Tetra-(2-butylthienyl)-4,4'-bispyranilidene,
2,2',6,6'-Tetra-(2-pentylthienyl)-4,4'-bispyranilidene,
2,2',6,6'-Tetra-(2-hexylthienyl)-4,4'-bispyranilidene,
2,2',6,6'-Tetrakis(7-methyl-2,3-dihydrothieno[3,4-b][1,4]dioxin-5-yl)-4,4'-bispyranilidene,
2,2',6,6'-Tetra-(2-heptylthienyl)-4,4'-bispyranilidene,
2,2',6,6'-Tetra-(2-methylthienyl)-4,4'-dithiobispyranilidene,
2,2',6,6'-Tetra-(2-ethylthienyl)-4,4'-dithiobispyranilidene,
2,2',6,6'-Tetra-(2-propylthienyl)-4,4'-dithiobispyranilidene,
2,2',6,6'-Tetra-(2-butylthienyl)-4,4'-dithiobispyranilidene,
2,2',6,6'-Tetra-(2-pentylthienyl)-4,4'-dithiobispyranilidene,
2,2',6,6'-Tetra-(2-hexylthienyl)-4,4'-dithiobispyranilidene,
2,2',6,6'-Tetra-(2-heptylthienyl)-4,4'-dithiobispyranilidene,
2,2',6,6'-Tetrakis(7-methyl-2,3-dihydrothieno[3,4-b][1,4]dioxin-5-yl)-4,4'-dithiobispyranilidene,
2,2',6,6'-Tetra-(2-methylthienyl)-4,4'-diselenobispyranilidene,
2,2',6,6'-Tetra-(2-ethylthienyl)-4,4'-diselenobispyranilidene,
2,2',6,6'-Tetra-(2-propylthienyl)-4,4'-diselenobispyranilidene,
2,2',6,6'-Tetra-(2-butylthienyl)-4,4'-diselenobispyranilidene,
2,2',6,6'-Tetra-(2-pentylthienyl)-4,4'-diselenobispyranilidene,
2,2',6,6'-Tetra-(2-hexylthienyl)-4,4'-diselenobispyranilidene,
2,2',6,6'-Tetra-(2-heptylthienyl)-4,4'-diselenobispyranilidene or
2,2',6,6'-Tetrakis(7-methyl-2,3-dihydrothieno[3,4-b][1,4]dioxin-5-yl)-4,4'-diselenobispyranilidene.

It is also an object of the invention to use at least one compound according to formula (I), wherein $X^1$ and $X^2$ are each independently selected from the group comprising oxygen, sulfur, and selenium, wherein $R^1$ and $R^2$ are each independently selected from the group comprising substituted thiophene and selenophene residues, as a light or IR absorber, in particular in an electronic or optoelectronic component.

"Light" is understood to mean electromagnetic radiation with a wavelength in the range from 380 nm to 780 nm. "Infrared (IR)" is understood to mean electromagnetic radiation with a wavelength in the range from 780 nm to 1 mm. "Near infrared (NIR)" is understood to mean electromagnetic radiation with a wavelength in the range from 780 nm to 3 µm.

A "light or IR absorber" is a compound that can absorb at least a portion of electromagnetic radiation with wavelengths in the range of 380 nm to 1 mm.

An "optoelectronic component" is understood to be a component that provides an interface between electrical and optical components. In embodiments, optoelectronic components are selected from the group consisting of organic solar cells (OSC), dye-sensitized solar cells (DSSC, Gratzel cell), organic integrated circuits (O-IC), organic field-effect transistors (OFET), organic thin film transistors (O-TFT), organic light emitting diodes (OLED), photodetectors and IR sensors, in particular infrared (IR) charge transfer (CT) absorption sensors.

In various embodiments, the use of at least one compound according to the invention as a light or IR absorber is carried out in combination with electron acceptors, preferably fullerenes, particularly preferably $C_{60}$- or $C_{70}$-fullerenes; or fullerene derivatives, such as 1-(3-methoxycarbonyl)-propyl-1-1-phenyl-(6,6)$C_{61}$ (PCBM) as photoactive mixed layers in optoelectronic components. Advantageously, after absorption of light or IR radiation by a compound according to the invention, a transfer of electrons to the electron acceptor takes place. Preferably, the electrons reach the electrode via an electron transport layer.

In further embodiments, the use occurs as donor absorber material in organic solar cells (OSC), as hole transport material (HTM) in dye-sensitized solar cells (DSSC, Gratzel cell), in organic integrated circuits (O-IC), in organic field effect transistors (OFET), in organic thin film transistors (O-TFT), in organic light emitting diodes (OLED), in photodetectors or in IR sensors, especially infrared (IR) charge transfer (CT) absorption sensors.

Preferably, the use of at least one compound according to the invention takes place in infrared (IR) charge transfer (CT) absorption sensors. Advantageously, IR CT absorption sensors with the compounds according to the invention achieve spectral line widths of at most 100 nm, preferably at most 50 nm, particularly preferably at most 15 nm.

It is also an object of the invention to use at least one compound according to formula (I), wherein $X^1$ and $X^2$ are each independently selected from the group comprising oxygen, sulfur, and selenium, wherein $R^1$ and $R^2$ are each independently selected from the group comprising substituted thiophene and selenophene residues, in a method of detecting an electromagnetic signal in the wavelength range from 780 nm to 10 µm.

Preferably, the use takes place in a method for the detection of an electromagnetic signal in the wavelength range from 780 nm to 10 µm comprising the steps:
  a) providing an optoelectronic component arranged on a substrate and
    i. comprising two separate and opposing mirror surfaces which form an optical microcavity,
    ii. comprising a photoactive layer arranged between the mirror surfaces and comprising at least one compound according to formula (I) and a further compound, wherein the further compound is preferably selected from fullerenes, preferably $C_{60}$ or $C_{70}$ fullerenes, or fullerene derivatives, preferably 1-(3-methoxycarbonyl)-propyl-1-1-phenyl-(6,6)$C_{61}$ (PCBM),
    wherein the energy difference between the HOMO energy of the compound according to formula (I) and the LUMO energy of the further compound is below 1.6 eV,
    wherein the optical path length between the mirror surfaces is in the range of 25 to 75% of the wavelength of the signal to be detected, and
    wherein the energy equivalent of the wavelength range of the electromagnetic signal to be detected lies in the range of
      the energy difference defined by the HOMO energy of the compound according to formula (I) and the LUMO energy of the further compound and the energy difference defined by the HOMO energy and the LUMO energy of the compound according to formula (I), wherein the photoactive layer is aligned, within the optical microcavity, in the spatial intensity maximum of the wavelength of the electromagnetic signal to be detected, between the mirror surfaces;

b) irradiating the optoelectronic component with an electromagnetic signal in the wavelength range of 780 nm to 10 μm;

c) amplifying the electromagnetic signal to be detected within the optical micro cavity, wherein, induced by the wavelength of the signal to be detected, a direct interchromophoric charge transfer from the first compound to the second compound takes place; and d) converting the electromagnetic signal into an electrical signal.

A further aspect of the invention relates to an electronic or optoelectronic component comprising at least one compound according to formula (I), wherein $X^1$ and $X^2$ are each independently selected from the group comprising oxygen, sulfur and selenium, wherein $R^1$ and $R^2$ are each independently selected from the group comprising substituted thiophene and selenophene residues.

In embodiments, the optoelectronic components further comprise at least one further compound, in particular an electron acceptor compound (acceptor compound), wherein the further compound is preferably selected from fullerenes, preferably $C_{60}$- or $C_{70}$-fullerenes, or fullerene derivatives, preferably 1-(3-methoxycarbonyl)-propyl-1-1-phenyl-(6,6)$C_{61}$ (PCBM). Preferably, the optoelectronic component has at least one compound according to the invention and at least one further compound as a photoactive blend layer.

In further embodiments, the optoelectronic component, in particular an organic solar cell, has two or more photoactive layers (multijunction components), the photoactive layers usually being accommodated in individual solar cells processed mostly vertically directly one above the other, which are connected in series via a so-called recombination contact.

In various embodiments, the optoelectronic component, in particular an organic solar cell, comprises the compounds of the invention as light absorbers in so-called cascade structures. In this case, the photoactive layer of the solar cell consists of a sequence of several donor molecules followed by several acceptor molecules (also in reverse order, depending on the embodiment as p-i-n or n-i-p structure). In other embodiments, multiple donors may also be mixed with multiple acceptors to form the photoactive layer in order to cover a broader spectral range of sunlight.

Advantageously, the intensity of the charge transfer of the optoelectronic component is two to three times greater than that of optoelectronic components comprising tetraphenyl-dipyranilidenes (TPDP).

In one embodiment, the optoelectronic components according to the invention have an absorption range with wavelengths up to at least 1000 nm, preferably up to at least 1300 nm, particularly preferably up to at least 1600 nm.

In preferred embodiments, the optoelectronic components according to the invention have an absorption range from 810 nm to 1665 nm, preferably from 900 nm to 1300 nm.

In further embodiments, the optoelectronic component comprises electrodes composed of metal, a conductive oxide, in particular indium tin oxide (ITO), ZnO:Al or another transparent conductive oxide (TCO); or a conductive polymer, in particular PEDOT/PSS (poly(3,4-ethylene-dioxy-thiophene)po-(styrenesulfonate)) or PANI (polyaniline).

In various embodiments, the electrode, which is disposed on a substrate, is translucent to light. "Translucency" is understood to mean a partial light transmission of a material, at least in a certain light wavelength range, with a transmission in the range from 1% to 100%.

In embodiments, the optoelectronic component comprises at least:
i. two separate and opposing mirror surfaces which form an optical microcavity,
ii. a photoactive layer arranged between the mirror surfaces and comprising at least one compound according to formula (I) and a further compound, wherein the further compound is preferably selected from fullerenes, preferably C60 or C70 fullerenes, or fullerene derivatives, preferably 1-(3-methoxycarbonyl)-propyl-1-1-phenyl-(6,6)C61 (PCBM), wherein the energy difference between the HOMO energy of the compound according to formula (I) and the LUMO energy of the further compound is below 1.6 eV, wherein the optical path length between the mirror surfaces is in the range of 25 to 75% of the wavelength of the signal to be detected, and wherein the energy equivalent of the wavelength range of the electromagnetic signal to be detected lies in the range of
the energy difference defined by the HOMO energy of the compound according to formula (I) and the LUMO energy of the further compound and
the energy difference defined by the HOMO energy and the LUMO energy of the compound according to formula (I), wherein the photoactive layer is aligned, within the optical microcavity, in the spatial intensity maximum of the wavelength of the electromagnetic signal to be detected, between the mirror surfaces, on a substrate.

Another aspect of the invention relates to the use of the optoelectronic component for the detection of an electromagnetic signal in the wavelength range from 780 nm to 10 μm with spatial, temporal and/or spectral resolution, and for further processing thereof.

For the realization of the invention, it is also expedient to combine the above-described embodiments and features of the claims, in particular to apply the above-described embodiments of the compound according to the invention to the described use and the described electronic or optoelectronic component.

In the following, the invention will be explained in more detail with reference to a number of embodiments and associated figures. The embodiments are intended to describe the invention without limiting its scope.

It is shown in

Figure 2:
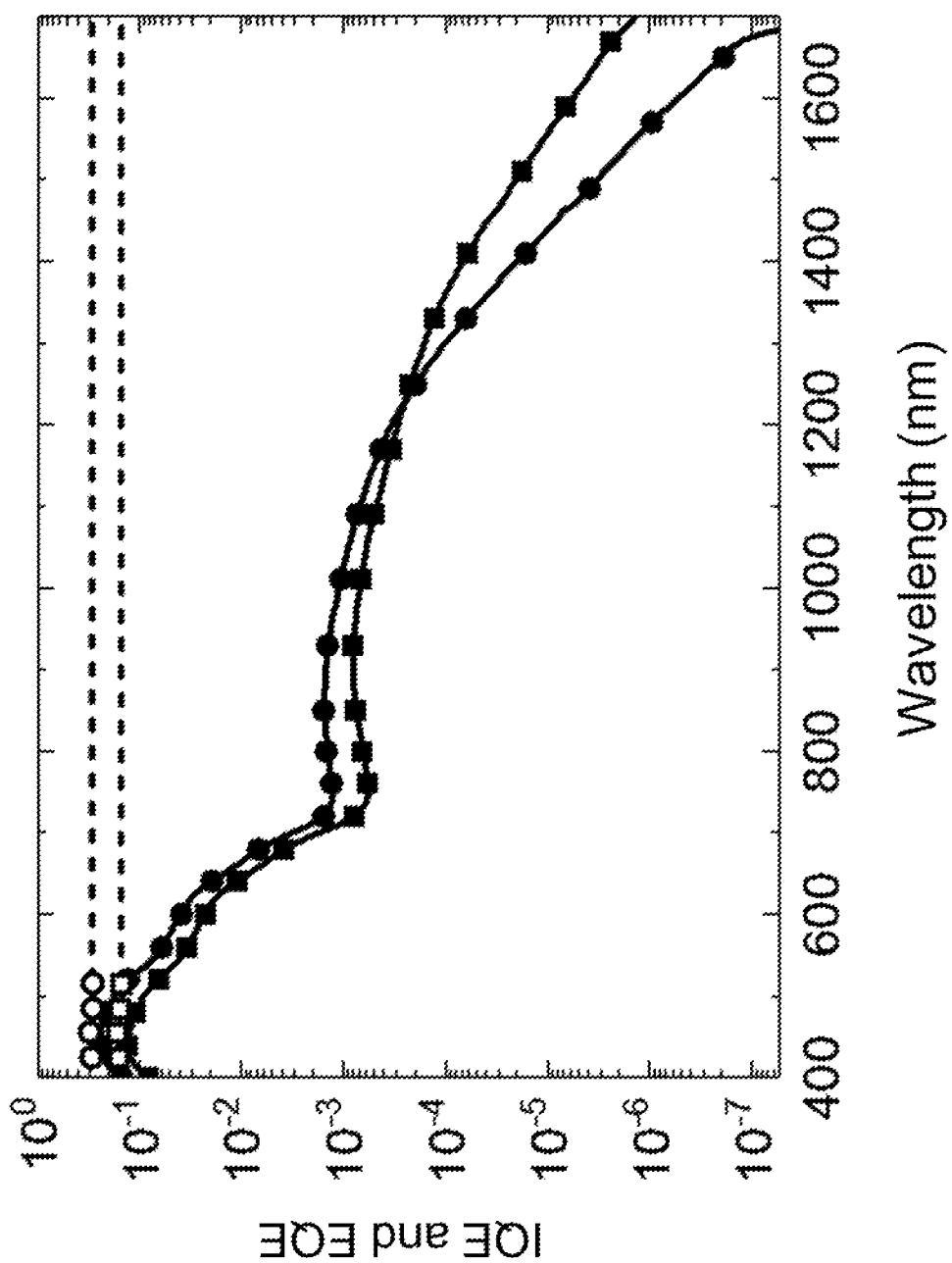
Figure 3:
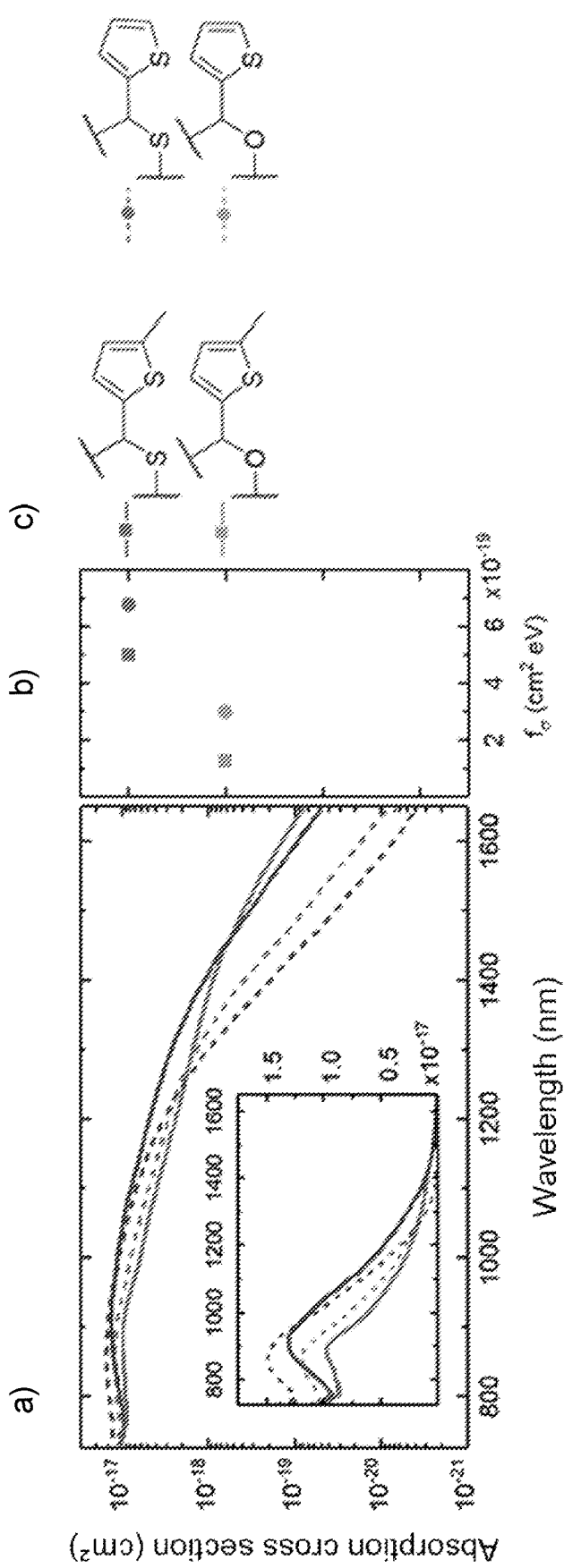

FIG. 1 the UV-Vis absorption spectra of thienyl-substituted bispyranylidene and dithiobispyranilidene in dimethylformamide (DMF) (c=10-5 mol/1);

FIG. 2 the measurement of the external quantum efficiency (EQE) and internal quantum efficiency (IQE) of optoelectronic devices comprising 2,2',6,6'-tetrathienyl-4,4'-dithiobispyranylidene (reference) (circles) or 2,2',6,6'-tetra(2-methylthienyl)-4,4'-dithiobispyranylidene (squares) and $C_{60}$. Unfilled characters represent the IQE in the spectral range from 425 nm to 525 nm (IQE=EQE absorbance[1]), the dashed line represents the average IQE, filled characters represent the EQE;

FIG. 3 a) the CT absorption profiles $\sigma_{CT}$ of the mixtures of the compounds with $C_{60}$ (linear and logarithmic scaling); b) oscillator strength $f_O$; c) structure of the symmetric thienyl-substituted bispyranylidenes and dithiobispyranilidenes.

GENERAL SYNTHESIS WORKING TECHNIQUES

Solvents are cleaned and dried before use according to standard techniques.
Electron Spray Ionization Mass Spectrometry, ESI-MS Mass spectrometry is performed using Bruker Esquire Ion Trap (ESI/APCI) and a sample concentration of 2 mg/l.
Nuclear Magnetic Resonance (NMR) Spectroscopy NMR spectra are measured using either a Bruker AC 300, AC 600 or a Bruker DRX 500 nuclear magnetic resonance spectrometer in deuterated solvents at 26 to 30° C. Shifts of the 1H and 13C resonances are given in ppm relative to the residual signal of the non-deuterated solvent. Coupling constants are given in Hz without indication of sign, using the following abbreviations for the multiplicities of the individual signals: s: Singlet; d: doublet; dd: doublet of doublets; t: triplet; qua: quartet; qi: quintet; sep: septet; m: multiplet; br.s.: broad signal.
Ultraviolet-Visible (UV-Vis) Absorption Spectroscopy Optical characterization is performed using UV-Vis spectroscopy to determine the optical bandwidth, the shape of the absorption band and the extinction coefficient. UV-Vis spectra are measured using a Perkin Elmer Lambda 25 UV/VIS spectrophotometer with a scan rate of 600 nm/min.

Synthesis recipe for 1,5-di-(2-thienyl)pentane-1,5-dione 15 ml of anhydrous dichloromethane (DCM) is added to 16.0 g (120 mmol, 2 eq.) of aluminum chloride in a 100 ml round-bottom flask under an inert gas atmosphere. Dropwise, a solution of 11.6 ml (120 mmol, 2.4 eq.) thiophene and 6.4 ml (50 mmol, 1 eq.) glutaryl chloride in 15 ml DCM is added over 10 min. Upon addition, the color changes from light orange to dark red. The solution is stirred overnight, and the flask is cooled in an ice bath. The reaction is stopped using ice and concentrated hydrochloric acid (2 ml). Water is added while stirring until the exothermic reaction with the excess aluminum chloride is completed. The mixture is diluted with 50 ml of DCM and stirred for 2 h. The organic phase is extracted with warm DCM, dried over magnesium sulfate and concentrated under vacuum. The crude product is ground and washed with cold diethyl ether.

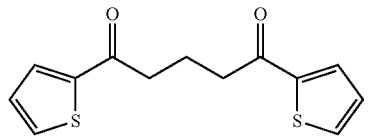 [SMILES: O=C(CCCC(=O)c1cccs1)c1cccs1]

Molecular formula: $C_{13}H_{12}O_2S_2$ (264.03 g/mol)
Yield: 11.2 g (42.3 mmol, 85%)
ESI-MS: m/z 265 [M]$^+$
$^1$H-NMR (500 MHz, CDCl$_3$, ppm): δ=7.73 (dd, J=3.8, 1.1 Hz, 1H), 7.61 (dd, J=4.9, 1.1 Hz, 1H), 7.10 (dd, J=4.9, 3.8 Hz, 1H), 3.04 (t, J=7.0 Hz, 2H), 2.19 (qt, J=7.0, 3.5 Hz, 1H).
$^{13}$C-NMR (75 MHz, CDCl$_3$, ppm): δ=193.39, 144.81, 134.22, 132.68, 128.78, 38.81, 19.96.

Synthesis recipe for 2,6-di-(2-thienyl)pyrylium tetrafluoroborate 9.7 ml (76.2 mmol, 10 eq.) tetrafluoroboric acid solution (50% (m/m) in water) is added dropwise over 30 min to a suspension of 2.0 g (7.6 mmol, 1 eq.) 1,5-di-(2-thienyl)pentane-1,5-dione in 50 ml acetic anhydride while maintaining the temperature below 15° C. using an ice bath. After the addition is complete, the mixture is stirred for another 2 h at room temperature and left overnight at 5° C. After the addition of 500 ml of hexane/diethyl ether (1:10), a brown precipitate precipitates. The product is obtained by vacuum filtration, washing with diethyl ether and vacuum drying at room temperature.

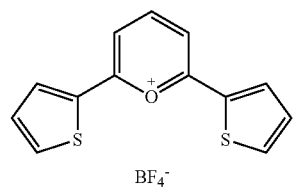

Molecular formula: $C_{13}H_9BF_4OS_2$ (332.01 g/mol)
Yield: 1.59 g (4.8 mmol, 63%)
ESI-MS: m/z 245 [M-BF$_4$]$^+$, 277 [M-BF$_4$+CH$_3$OH]$^+$
Absorption (DCM): $\alpha_{max}$=489 nm (ε=30458 Lmol$^{-1}$cm$^{-1}$)
$^1$H-NMR (500 MHz, acetonitrile, ppm): δ=8.61 (t, J=8.4 Hz, 1H), 8.28 (dd, J=4.0, 1.1 Hz, 2H), 8.21 (dd, J=4.9, 1.1 Hz, 2H), 8.08 (d, J=8.4 Hz, 2H), 7.44 (dd, J=4.9, 4.1 Hz, 2H).
$^{13}$C-NMR (75 MHz, acetonitrile, ppm): δ=167.00, 155.90, 140.54, 186.98, 188.28, 181.95, 117.71.

Synthesis recipe for 2,2',6,6'-tetrathienyl-4,4'-bispyranylidene

Under an inert gas atmosphere, 1.2 ml (4.7 mmol, 1 eq.) of tributyl phosphine is added to an orange suspension of 1.56 g (4.7 mmol, 1 eq.) of 2,6-di-(2-thienyl)pyrylium tetrafluoroborate in 50 ml of dried acetonitrile. The mixture changes color to yellow and is stirred for 2.5 h at room temperature. Then 4.0 ml (23.5 mmol, 5 eq.) of N,N-diisopropylethylamine is added. The mixture is refluxed at 95° C. for 2 h under an inert gas atmosphere and allowed to stand overnight. The product is obtained as a black solid after filtration, washing with acetonitrile and drying in air.

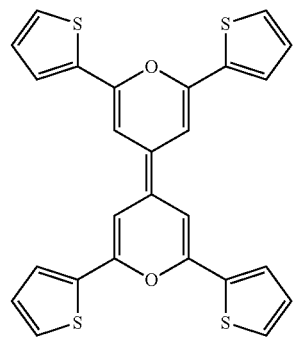 [SMILES: C1=C(c2cccs2)OC(c2cccs2)=CC1=C1C=C(c2cccs2)OC(c2cccs2)=C1]

Molecular formula: $C_{26}H_{16}O_2S_4$ (488.00 g/mol)

Yield: 0.62 g (1.27 mmol, 54%)

ESI-MS: m/z 488 [M]$^+$

Absorption (DMF): $\alpha_{max}$=482 nm ($\varepsilon$=29610 Lmol$^{-1}$cm$^{-1}$)

Melting point: 239° C.

$^1$H-NMR (500 MHz, CDCl$_3$, ppm): $\delta$=7.74 (dd, J=3.7, 1.1 Hz, 1H), 7.65 (dd, J=5.0, 1.1 Hz, 1H), 7.21 (dd, J=5.0, 3.7 Hz, 1H), 6.95 (s, 1H).

$^{13}$C-NMR (125.75 MHz, CDCl$_3$, ppm): $\delta$=144.90, 136.50, 12.08, 126.42, 124.15, 113.68, 101.85.

Synthesis recipe for 2,6-dithienylthiopyrylium perchlorate 7.80 g (29.5 mmol, 1.0 eq.) 1,5-di-(2-thienyl)pentane-1,5-dione, 9.86 g (44.3 mmol, 1.5 eq.) phosphorus(V) sulfide, 180 ml acetic acid, and 18.90 g (60 mmol, 6.0 eq.) lithium perchlorate are successively introduced into a 250 ml round-bottom flask. The mixture is boiled for 3 h under reflux. The color changes from orange to dark red. A green solid is obtained by filtration and washing with hot acetic acid. The filtrate is concentrated under vacuum and a black solid is obtained by adding an excess of diethyl ether and storing at 5° C. overnight. The crude product is recrystallized in acetic acid to obtain green crystals.

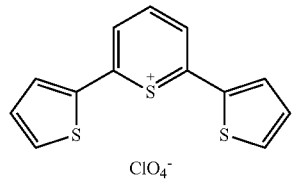

Molecular formula: $C_{13}H_9ClO_4S_3$ (359.94 g/mol)

Yield: 3.0 g (8.3 mmol, 28%)

ESI-MS: m/z 261 [M-ClO$_4$]$^+$

Absorption (DCM): $\alpha_{max}$=514 nm ($\varepsilon$=31902 Lmol$^{-1}$cm$^{-1}$)

$^1$H-NMR (500 MHz, Acetonitril, ppm): $\delta$=8.55 (t, J=8.8 Hz, 1H), 8.43 (d, J=8.7 Hz, 2H), 8.20-8.04 (m, 4H), 7.42 (dd, J=4.9, 4.0 Hz, 2H).

$^{13}$C-NMR (125.75 MHz, Acetonitril, ppm): $\delta$=162.24, 151.35, 139.07, 137.80, 134.81, 132.50, 130.26.

Synthesis recipe for 2,2',6,6'-tetrathienyl-4,4'-dithio-bispyranylidene (reference)

Under an inert gas atmosphere, 0.65 ml (2.6 mmol, 1 eq.) of tributyl phosphine is added to a violet suspension of 0.95 g (2.6 mmol, 1 eq.) of 2,6-dithienylthiopyrylium perchlorate in 50 ml of dried acetonitrile. The mixture changes color to gray and is stirred for 2.5 h at room temperature. Then 2.2 ml (13.0 mmol, 5 eq.) of N,N-diisopropylethylamine is added. The mixture is boiled under reflux at 95° C. for 2 h under an inert gas atmosphere and allowed to stand overnight. The product is obtained as a black solid after filtration and recrystallization from DMSO.

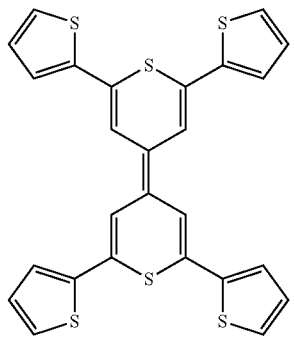 [SMILES: C1=C(c2cccs2)SC(c2cccs2)=CC1=C1C=C(c2cccs2)SC(c2cccs2)=C1]

Molecular formula: $C_{26}H_{16}S_6$ (519.96 g/mol)

Yield: 0.26 g (0.5 mmol, 39%)

ESI-MS: m/z 520 [M]$^+$

Absorption (DMF): $\alpha_{max}$=512 nm

Melting point: 314° C.

$^1$H-NMR (500 MHz, pyridine, ppm): $\delta$=7.52 (dd, J=5.1, 1.1 Hz, 1H), 7.50 1 7.46 (m, 1H), 7.40 (s, 1H), 7.13 (dd, J=5.1, 3.7 Hz, 1H).

Synthesis recipe for 1,5-di-(2-(5-methyl)thienyl)pentane-1,5-dione 15 ml of anhydrous dichloromethane (DCM) is added to 16.0 g (120 mmol, 2 eq.) of aluminum chloride in a 100 ml round-bottom flask under an inert gas atmosphere. Dropwise, a solution of 11.6 ml (120 mmol, 2.4 eq.) 2-methyl-thiophene and 6.4 ml (50 mmol, 1 eq.) glutaryl chloride in 15 ml DCM is added over 10 min. Upon addition, the color changes from light orange to dark red. The solution is stirred overnight, and the flask is cooled in an ice bath. The reaction is stopped using ice and concentrated hydrochloric acid (2 ml). Water is added while stirring until the exothermic reaction with the excess aluminum chloride is completed. The mixture is diluted with 50 ml of DCM and stirred for 2 h. The organic phase is removed. The organic phase is extracted with warm DCM, dried over magnesium sulfate, and concentrated under vacuum. The crude product is ground and washed with cold diethyl ether.

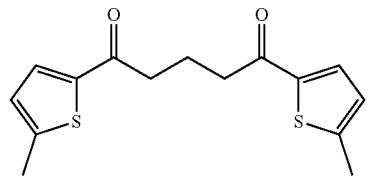 [SMILES: Cc1ccc(C(=O)CCCC(=O)c2ccc(C)s2)s1]

Molecular formula: $C_{15}H_{16}O_2S_2$ (292.06 g/mol)

Yield: 9.9 g (33.8 mmol, 68%)

ESI-MS: m/z 293 [M]$^+$ $^1$H-NMR (500 MHz, CDCl$_3$, ppm): $\delta$=7.53 (d, J=3.7 Hz, 1H), 6.76 (m, 1H), 2.94 (t, J=7.0 Hz, 2H), 2.51 (d, J=0.7 Hz, 3H), 2.13 (p, J=7.0 Hz, 1H).

$^{13}$C-NMR (125.75 MHz, CDCl$_3$, ppm): $\delta$=192.47, 149.60, 141.96, 132.64, 126.74, 37.75, 19.72, 15.60.

Synthesis recipe for 2,6-di-(2-(5-methyl)thienyl)pyrylium tetrafluoroborate 9.7 ml (76.2 mmol, 10 eq.) tetrafluoroboric acid solution (50% (m/m) in water) is added dropwise over 30 min to a suspension of 2.2 g (7.6 mmol, 1 eq.) 1,5-di-(2-(5-methyl)thienyl)pentane-1,5-dione in 50 ml acetic anhydride while the temperature is maintained below 15° C. using an ice bath. After the addition is complete, the mixture is stirred for another 2 h at room temperature and left overnight at 5° C. After the addition of 500 ml of hexane/diethyl ether (1:10), a red precipitate precipitates. The product is obtained by vacuum filtration, washing with diethyl ether, and vacuum drying at room temperature.

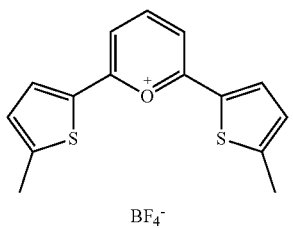

Molecular formula: $C_{15}H_{13}BF_4OS_2$ (360.04 g/mol)
Yield: 1.0 g (2.8 mmol, 37%)
ESI-MS: m/z 273 $[M-BF_4]^+$, 305 $[M-BF_4+CH_3OH]^+$
Absorption (DCM): $\alpha_{max}$=520 nm ($\epsilon$=27691 $Lmol^{-1}cm^{-1}$)
$^1$H-NMR (500 MHz, Acetonitril, ppm): $\delta$=8.45 (t, J=8.4 Hz, 1H), 8.06 (d, J=4.0 Hz, 2H), 7.88 (d, J=8.4 Hz, 2H), 7.13 (dd, J=4.0, 0.9 Hz, 2H), 2.66 (s, 6H).
$^{13}$C-NMR (75 MHz, acetonitrile, ppm): $\delta$=166.03, 157.53, 154.45, 137.45, 131.13, 130.83, 116.23, 16.58.

Synthesis recipe for 2,2',6,6'-tetra-(2-methylthienyl)-4,4'-bispyranylidene

Under an inert gas atmosphere, 1.2 ml (4.7 mmol, 1 eq.) of tributylphosphine is added to an orange suspension of 1.69 g (4.7 mmol, 1 eq.) of 2,6-di-(2-(5-methyl)thienyl)pyrylium tetrafluoroborate in 50 ml of dried acetonitrile. The mixture changes color to yellow and is stirred for 2.5 h at room temperature. Then 4.0 ml (23.5 mmol, 5 eq.) of N,N-diisopropylethylamine is added. The mixture is boiled under reflux at 95° C. for 2 h under an inert gas atmosphere and allowed to stand overnight.

The product is obtained as a black solid after filtration, washing with acetonitrile and drying in air.

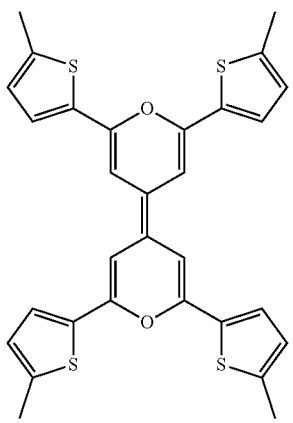 [SMILES: Cc1ccc(C2=CC(=C3C=C(c4ccc(C)s4)OC(c4ccc(C)s4)=C3)C=C(c3ccc(C)s3)O2)s1]

Molecular formula: $C_{30}H_{24}O_2S_4$ (544.07 g/mol)
Yield: 0.89 g (1.64 mmol, 70%)
HR-EI-MS: m/z 544.0661 $[M]^+$
Absorption (DMF): $\alpha_{max}$=488 nm ($\epsilon$=44663 $Lmol^{-1}cm^{-1}$)
Melting point: 328° C.
$^1$H-NMR (600 MHz, Benzol, ppm): $\delta$=7.16 (s, 1H), 6.45 (d, J=3.0 Hz, 1H), 6.40 (br.s., 1H), 2.11 (br.s., 3H).

Synthesis recipe for 2,6-di(5-methylthienyl)thiopyrylium perchlorate 5.00 g (17.1 mmol, 1.0 eq.) 1,5-di-(2-(5-methyl)thienyl)pentane-1,5-dione, 5.72 g (25.7 mmol, 1.5 eq.) phosphorus (V) sulfide, 250 ml acetic acid, and 10.90 g (102.2 mmol, 6.0 eq.) lithium perchlorate are successively introduced into a 250 ml round-bottom flask. The mixture is boiled for 3 h under reflux. The color changes from orange to deep purple. The mixture is hot filtered and allowed to stand for 48 h. The mixture is refluxed. The green crystals are washed with diethyl ether and dried in air.

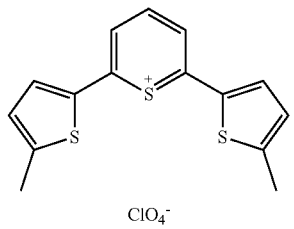

Molecular formula: $C_{15}H_{13}ClO_4S_3$ (387.97 g/mol)
Yield: 2.16 g (5.6 mmol, 33%)
ESI-MS: m/z 289 $[M-ClO_4]^+$
Absorption (DCM): $\alpha_{max}$=552 nm ($\epsilon$=37946 $Lmol^{-1}cm^{-1}$)
$^1$H-NMR (500 MHz, acetonitrile, ppm): $\delta$=3.33 (dd, J=9.5, 3.1 Hz, 1H), 3.25 4 3.15 (m, 2H), 7.93 (d, J=4.0 Hz, 2H), 7.13 (dd, J=4.0, 1.0 Hz, 2H), 2.65 (s, 6H).
$^{13}$C-NMR (75 MHz, acetonitrile, ppm): $\delta$=161.09, 156.02, 150.44, 135.56, 135.27, 131.57, 123.49, 16.76.

Synthesis recipe for 2.2',6,6'-tetra(2-methylthienyl)-4,4'-dithiobispyranylidene Under an inert gas atmosphere, 0.7 ml (2.8 mmol, 1 eq.) of tributyl phosphine is added to a violet suspension of 1.10 g (2.8 mmol, 1 eq.) of 2,6-di(5-methylthienyl)thiopyrylium perchlorate in 50 ml of dried acetonitrile. The mixture changes color to gray and is stirred for 2.5 h at room temperature. Then 2.4 ml (14.0 mmol, 5 eq.) of N,N-diisopropylethylamine is added. The mixture is boiled under reflux at 95° C. for 2 h under an inert gas atmosphere and allowed to stand overnight. The product is obtained as a black solid after filtration and recrystallization from DMSO.

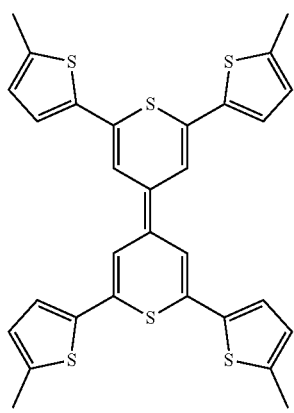 [SMILES: Cc1ccc(C2=CC(=C3C=C(c4ccc(C)s4)SC(c4ccc(C)s4)=C3)C=C(c3ccc(C)s3)S2)s1]

Molecular formula: C$_{30}$H$_{24}$S$_6$ (576.02 g/mol)

Yield: 0.58 g (1.0 mmol, 72%)

ESI-MS: m/z 576 [M]$^+$

Absorption (DMF): α$_{max}$=521 nm

Melting point: 304° C.

$^1$H-NMR (500 MHz, pyridine, ppm): δ=7.35 (m, 1H), 7.29 (d, J=3.6 Hz, 1H), 6.76 (dd, J=3.6, 1.1 Hz, 1H), 2.33 (s, 3H).

Synthesis recipe for 1,5-di-(2-(5-ethyl)thienyl)pentane-1,5-dione 15 ml of anhydrous dichloromethane (DCM) is added to 16.0 g (120 mmol, 2 eq.) of aluminum chloride in a 100 ml round-bottom flask under an inert gas atmosphere. Dropwise, a solution of 12.7 ml (120 mmol, 2.4 eq.) 2-ethylthiophene and 6.4 ml (50 mmol, 1 eq.) glutaryl chloride in 15 ml DCM is added over 10 min. Upon addition, the color changes from light orange to dark red. The solution is stirred overnight, and the flask is cooled in an ice bath. The reaction is stopped using ice and concentrated hydrochloric acid (2 ml). Water is added while stirring until the exothermic reaction with the excess aluminum chloride is completed. The mixture is diluted with 50 ml of DCM and stirred for 2 h. The organic phase is removed. The organic phase is extracted with warm DCM, dried over magnesium sulfate, and concentrated under vacuum. The crude product is ground and recrystallized from diethyl ether.

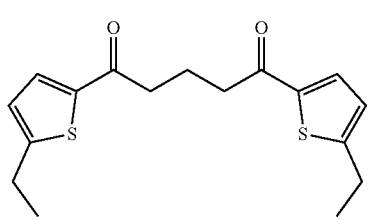 [SMILES: CCc1ccc(C(=O)CCCC(=O)c2ccc(CC)s2)s1]

Molecular formula: C$_{17}$H$_{20}$O$_2$S$_2$ (320.09 g/mol)

Yield: 10.3 g (32.1 mmol, 64%)

ESI-MS: m/z 321 [M]$^+$ $^1$H-NMR (500 MHz, CDCl$_3$, ppm): δ=7.55 (d, J=3.8 Hz, 1H), 6.79 (dt, J=3.8, 0.9 Hz, 1H), 2.95 (t, J=7.0 Hz, 2H), 2.85 (qd, J=7.5, 0.6 Hz, 2H), 2.14 (p, J=7.0 Hz, 1H), 1.30 (t, J=7.5 Hz, 3H).

$^{13}$C-NMR (75 MHz, CDCl$_3$, ppm): δ=192.52, 157.16, 141.46, 132.47, 124.90, 37.76, 24.00, 19.74, 15.53.

Synthesis recipe for 2,6-di-(2-(5-ethyl)thienyl)pyrylium tetrafluoroborate 9.7 ml (76.2 mmol, 10 eq.) tetrafluoroboric acid solution (50% (m/m) in water) is added dropwise over 30 min to a suspension of 2.4 g (7.6 mmol, 1 eq.) 1,5-di-(2-(5-ethyl)thienyl)pentane-1,5-dione in 50 ml acetic anhydride while the temperature is maintained below 15° C. using an ice bath. After the addition is complete, the mixture is stirred for another 2 h at room temperature and left overnight at 5° C. After the addition of 500 ml of hexane/diethyl ether (1:10), a red precipitate precipitates. The product is obtained by vacuum filtration, washing with diethyl ether and vacuum drying at room temperature.

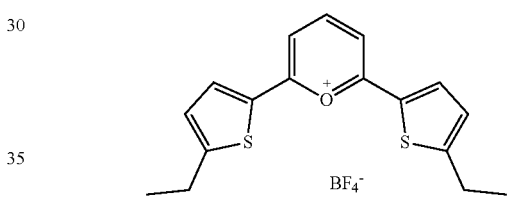

Molecular formula: C$_{17}$H$_{17}$BF$_4$OS$_2$ (388.07 g/mol)

Yield: 1.4 g (3.6 mmol, 48%)

ESI-MS: m/z 301 [M-BF$_4$]$^+$

Absorption (DCM): α$_{max}$=524 nm (ε=31596 Lmol$^{-1}$cm$^{-1}$)

$^1$H-NMR (500 MHz, Acetonitril, ppm): δ=8.45 (t, J=8.4 Hz, 1H), 8.11 (d, J=4.1 Hz, 2H), 7.89 (d, J=8.4 Hz, 2H), 7.20 (dt, J=4.1, 0.9 Hz, 2H), 3.05 (q, J=7.5 Hz, 4H), 1.39 (t, J=7.5 Hz, 6H).

$^{13}$C-NMR (75 MHz, Acetonitril, ppm): δ=165.95, 164.53, 154.10, 137.05, 130.22, 129.13, 115.99, 24.79, 15.56.

Synthesis recipe for 2,2',6,6'-tetra-(2-ethylthienyl)-4,4'-bispyranylidene

Under an inert gas atmosphere, 1.3 ml (5.2 mmol, 1 eq.) tributylphosphine is added to an orange suspension of 2.0 g (5.2 mmol, 1 eq.) 2,6-di-(2-(5-ethyl)thienyl)pyrylium tetrafluoroborate in 60 ml dried acetonitrile. The mixture changes color to yellow and is stirred for 2.5 h at room temperature. Then 4.4 ml (26 mmol, 5 eq.) of N,N-diisopropylethylamine is added. The mixture is boiled under reflux at 95° C. for 2 h under an inert gas atmosphere and allowed to stand overnight. The product is obtained as a black solid after filtration, washing with acetonitrile and drying in air.

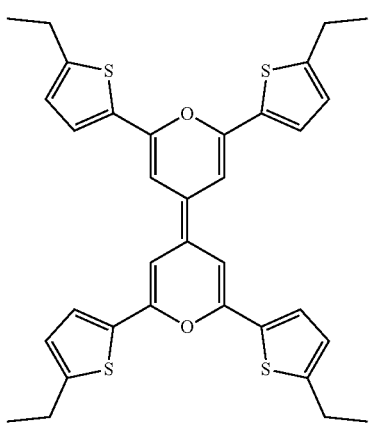 [SMILES: CCc1ccc(C2=CC(=C3C=C(c4ccc(CC)s4)OC(c4ccc(CC)s4)=C3)C=C(c3ccc(CC)s3)O2)s1]

Molecular formula: C$_{34}$H$_{32}$O$_2$S$_4$ (600.13 g/mol)
Yield: 1.0 g (1.67 mmol, 64%)
HR-EI-MS: m/z 600.1288 [M]$^+$
Absorption (DMF): α$_{max}$=488 nm (ε=51749 Lmol$^{-1}$cm$^{-1}$)
Melting point: 221° C.
$^1$H-NMR (500 MHz, benzene, ppm): δ=7.16 (s, 1H), 6.52 (d, J=3.5 Hz, 1H), 6.44 (br.s., 1H), 2.53 (br.s., 2H), 1.07 (t, J=7.6 HZ, 3H).

Synthesis recipe for
2,6-di(5-ethylthienyl)thiopyrylium perchlorate 4.00 g (12.6 mmol, 1.0 eq.) 1,5-di-(2-(5-ethyl)thienyl)pentane-1,5-dione, 4.21 g (18.9 mmol, 1.5 eq.) phosphorus (V) sulfide, 250 ml acetic acid, and 8.07 g (75.6 mmol, 6.0 eq.) lithium perchlorate are successively introduced into a 250 ml round-bottom flask. The mixture is boiled for 3 h under reflux. The color changes from orange to deep purple. The mixture is hot filtered and allowed to stand for 48 h. The mixture is refluxed. The green crystals are washed with diethyl ether and dried in air.

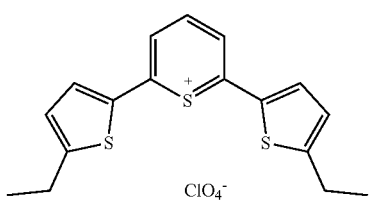

Molecular formula: C$_{17}$H$_{17}$ClO$_4$S$_3$ (416.00 g/mol)
Yield: 2.23 g (5.4 mmol, 43%)
ESI-MS: m/z 317 [M-ClO$_4$]$^+$
Absorption (DCM): α$_{max}$=554 nm (ε=39270 Lmol$^{-1}$cm$^{-1}$)
$^1$H-NMR (300 MHz, Acetonitril, ppm): δ=8.39 (dd, J=9.6, 3.0 Hz, 1H), 8.26-8.16 (m, 2H), 7.95 (d, J=4.0 Hz, 2H), 7.18 (dt, J=4.0, 0.9 Hz, 2H), 3.01 (q, J=7.5 Hz, 4H), 1.37 (t, J=7.5 Hz, 6H).
$^{13}$C-NMR (125.75 MHz, CDCl$_3$, ppm): δ=161.92, 159.34, 149.72, 134.38, 133.70, 128.64, 126.94, 24.42, 15.28.

Synthesis recipe for 2,2',6,6'-tetra(2-ethylthienyl)-4,4'-dithiobispyranylidene

Under an inert gas atmosphere, 0.6 ml (2.4 mmol, 1 eq.) of tributyl phosphine is added to a violet suspension of 1.0 g (2.4 mmol, 1 eq.) of 2,6-di(5-ethylthienyl)thiopyrylium perchlorate in 50 ml of dried acetonitrile. The mixture changes color to gray and is stirred for 2.5 h at room temperature. Then 2.1 ml (12.0 mmol, 5 eq.) of N,N-diisopropylethylamine is added. The mixture is boiled under reflux at 95° C. for 2 h under an inert gas atmosphere and allowed to stand overnight. The product is obtained in the form of black crystals after filtration, washing with acetonitrile and drying in air.

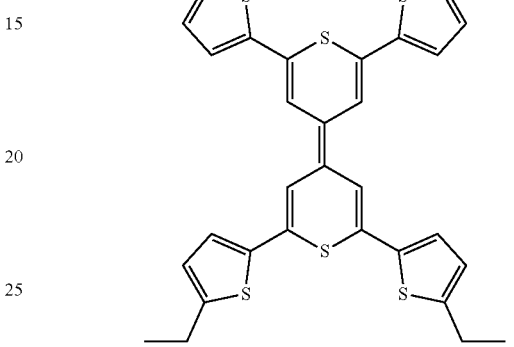

Molecular formula: C$_{34}$H$_{32}$S$_6$ (632.08 g/mol)
Yield: 0.46 g (0.73 mmol, 61%)
ESI-MS: m/z 632 [M]$^+$
Absorption (DMF): α$_{max}$=521 nm (ε=72122 Lmol$^{-1}$cm$^{-1}$)
Melting point: 253° C.
$^1$H-NMR (500 MHz, pyridine, ppm): δ=7.41 (s, 1H), 7.34 (d, J=3.6 Hz, 1H), 6.80 (d, J=3.6 Hz, 1H), 2.70 (q, J=7.5 Hz, 2H), 1.17 (t, J=7.5 Hz, 3H).
$^{13}$C-NMR (125.75 MHz, benzene, ppm): δ=147.99, 139.99, 127.12, 125.02, 124.74, 124.42, 119.13, 24.16, 16.34.

FIG. 1 shows the UV-Vis absorption spectra of the thienyl-substituted bispyranylidenes and dithiobispyranilidenes in dimethylformamide (DMF). The curves are normalized to the strongest π-π* transition in each case. For the thienyl-substituted bispyranylidenes, the absorption band is split into two peaks and exhibits two red-shifted shoulders of low intensity. The thienyl-substituted dithiobispyranilidenes exhibit an absorption band with an approximately 100 nm red-shifted λ$_{max}$ compared to the equivalent thienyl-substituted bispyranylidenes. Furthermore, the methyl- or ethyl-substituted thienyl compounds exhibit a red shift compared to the unsubstituted thienyl compounds.

Synthesis recipe for 1,5-bis(7-methyl-2,3-dihydrothieno[3,4-b][1,4]dioxin-5-yl)pentane-1,5-dione 2.33 g AlCl$_3$ is suspended with 20 ml dry DCM under intense stirring and cooled with ice. Under ice cooling, a solution of 2.72 g 5-methyl-2,3-dihydrothieno[3,4-b][1,4]dioxin-5-yl, 1.4 g glutaryl chloride and 20 ml DCM is slowly added. Subsequently, stirring is continued for 24 h at room temperature.

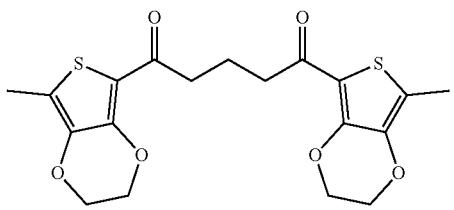

Molecular formula: $C_{19}H_{20}O_6S_2$ (408.48 g/mol)
Yield: 2.7 g (80%)
ESI-MS: m/z 409.1 [MH]$^+$ Synthesis recipe for 2,6-bis(7-methyl-2,3-dihydrothieno[3,4-b][1,4]dioxin-5-yl])-thiopyrylium-perchlorate 2.5 g of 1,5-bis(7-methyl-2,3-dihydrothieno[3,4-b][1,4]dioxin-5-yl])pentane-1,5-dione, 2.1 g of P2S10, and 3.9 g of LiClO4 are heated in 80 ml of glacial acetic acid for 3 h under reflux. After cooling and allowing to stand overnight, a purple solid is aspirated and washed with ether.

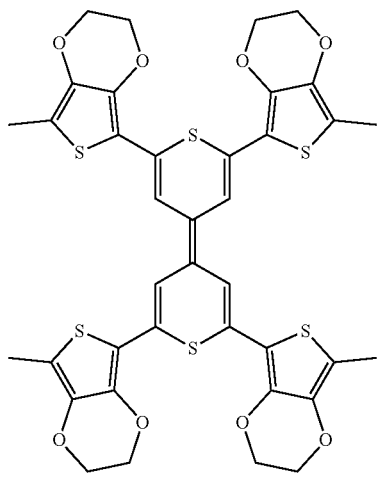

Molecular formula: $C_{38}H_{32}O_8S_6$ (809.03 g/mol)
Yield: 0.88 g (73%)
ESI-MS: m/z 808.1 [M]$^+$ General Procedure for the Synthesis of Diselenobispyranilidenes Diselenobispyranilidenes are accessible, for example, via selenopyranthiones from selenopyranones (Detty et al. 1985). 10 mmol of a corresponding selenopyranothione and 3 g of copper powder are heated at reflux for 16 h in 30 ml of toluene under stirring as well as inert gas. The reaction mixture is subjected to suitable workup and recrystallized from acetonitrile.

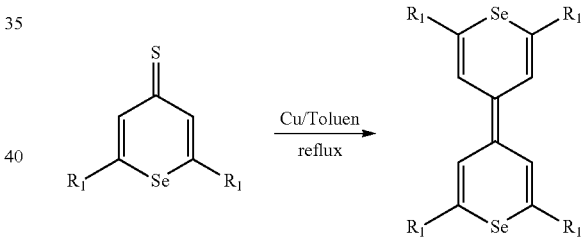

General Procedure for the Synthesis of Unsymmetrical Bispyranilidenes

Unsymmetrical bispyranilidenes can be synthesized analogously to the symmetrical compounds via phosphonium salts in a two-step reaction according to Reynolds and Chen (Reynolds and Chen 1980). The thio(seleno)pyrylium salt can also be phosphonylated and then reacted with the pyrylium salt.

A solution of 10 mmol pyrylium salt in 25 ml acetonitrile is stirred at room temperature for 2 h until the intense yellow color disappears. The white precipitate is aspirated and washed with acetonitrile.

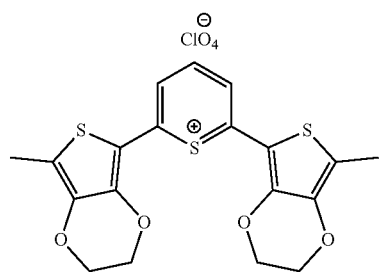

Molecular formula: $C_{19}H_{17}ClOS_3$ (504.98 g/mol)
Yield: 1.92 g (77%)
ESI-MS: m/z 405.1 [M-ClO$_4$]$^+$ 2,2',6,6'-Tetrakis(7-methyl-2,3-dihydrothieno[3,4-b][1,4]dioxin-5-yl)-4,4'-dithiobispyranilidene 1.5 g of the corresponding thiopyrylium salt is dissolved in 40 ml of acetonitrile under N$_2$ purge, and 0.73 ml of PBu$_3$ is added. This mixture is stirred for 2 h at room temperature, 1.5 ml of Hünig's base is added and heated for 2 h under reflux. After cooling, crystals are formed, which are aspirated and washed with a suitable solvent.

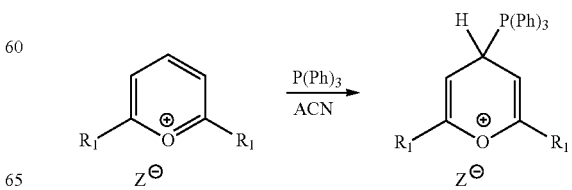

In a second step, a suspension of 2 mmol of the corresponding phosphonium salt shown previously is cooled to −78° C. in 35 ml of THF under inert gas with stirring. 0.9 ml of 2.5 M n-BuLi is added slowly and stirred for another 5 min. Then, 2 mmol of the desired thio- or selenopyrylium salt is added and stirred for 1 h at −78° C. followed by the addition of 5 ml of triethylamine. The reaction mixture is slowly warmed to room temperature overnight and purified chromatographically. Good to very good yields can be achieved.

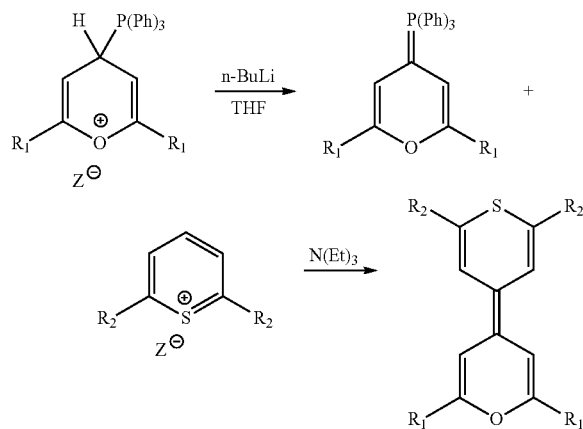

Process for Trifluoromethylation

Negishi et al. describe a process for trifluoromethylation, whereby the compounds of the invention are prepared with perfluoroalkyl residues (Negishi et al. 2016).

Electrochemical Characterization

Cyclic Voltammetry, CV

Cyclic voltammetry using a potentiostat (Methrom, µ-Autolab) and a 3-electrode cell configuration is performed to measure oxidation and reduction potentials and further determine HOMO/LUMO energy levels. Tetrabutylammonium hexafluorophosphate in dried dimethylformamide (DMF) or dimethyl sulfoxide (DMSO) (0.1 M) is used as the electrolyte, a glass-platinum electrode is used as the working electrode, a platinum wire is used as the counter electrode, and Ag/AgCl is used as the pseudo-reference electrode. Ferrocene/ferrocenium is used as an internal standard to scale the measured potentials. All solvents are deoxygenated with nitrogen before measurement. The measurement is made in the range of −1 V to 1 V, with a scan rate of 50 mV/s and 100 mV/s. The sample is measured with a concentration of 1 mM/l.

Differential Scanning Calorimetry, DSC

Thermal characterization is performed by differential scanning calorimetry (DSC) to determine phase transitions, melting and decomposition temperatures. DSC is performed using Mettler-Toledo DSC 1 Star and a scan rate of 5 K/min under a nitrogen atmosphere.

Sublimation

The compounds are crystallized two to three times to increase purity. Sublimation is carried out by means of a 3-zone gradient furnace from VEB Hochvakuum Dresden.

Fabrication of the Optoelectronic Component

The optoelectronic component is fabricated, for example, by thermal evaporation under ultra-high vacuum (8 to 10 mbar) onto a glass substrate with a pre-patterned ITO contact (Thin Film Devices, USA). A layer of 4, 7-diphenyl-1,10-phenanthroline (BPhen):Cs, C60, 2,2',6,6'-tetrathienyl-4,4'-dithiobispyranylidene or 2,2',6,6'-tetra(2-methylthienyl)-4,4'-dithiobispyranylidene:C60 (mixture 5% (m/m) in C60), N4,N4'-bis(9,9-dimethyl-9H-265-fluoren-2-yl)-N4,N4'-diphenylbiphenyl-4,4'-diamine (BF-DPB):F6-TCNNQ, 2,2'-(perfluoronaphthalene-2,6-diylidene)dimalononitrile (F6-TCNNQ) and Al is deposited on top. The device is characterized by the geometrical overlap of the lower and upper contacts with 6.44 m2. The organic region is bonded to a small glass substrate.

Sensitive External Quantum Efficiency (EQE) Measurements

External quantum efficiencies are measured using a monochromatic light source to generate a current in an organic solar cell (OSC) under short-circuit conditions. The resulting current is pre-amplified and analyzed using a lock-in amplifier (Signal Recovery 7280 DSP).

FIG. 2 shows the results of measuring the external quantum efficiency (EQE) and internal quantum efficiency (IQE) of the optoelectronic devices comprising mixtures of 2,2',6,6'-tetrathienyl-4,4'-dithiobispyranylidene (reference) (circles) and 2,2',6,6'-tetra(2-methylthienyl)-4,4'-dithiobispyranylidene (squares), respectively, and Ceo. The IQE was calculated in the spectral range from 425 nm to 525 nm (IQE=EQE−absorbance$^{-1}$), and an average IQE was calculated assuming that the IQE is independent of the excitation wavelength.

Using the IQE and the density of the donor molecules in the 50 nm thin films, the EQE spectra are converted to the $6C_T$ absorption profiles (FIG. 3). The methylated compounds show red-shifted CT absorption compared to the equivalent non-methylated compounds. The introduction of sulfur into the pyranilidene core increases the peak $\sigma_{CT}$ and $f_o$ up to twofold.

CITED NON-PATENT LITERATURE

Bolag A, Mamada M, Nishida J, Yamashita Y (2009) Field-Effect Transistors Based on Tetraphenyldipyranylidenes and the Sulfur Analogues. Chem. Mater. 21, 4350-4352.

Detty M R, Hassett J W, Murray B J, Reynolds G A (1985) Δ$^{4,4}$-4-Chalcogenpyranyl-4H-Chalcogenapyrans. Tetrahedron 41, 4853-4859.

Fabre C, Fugnitto R, Strzelecka H (1976) Sur la synthèse de dipyranylidènes. Comptes rendus des séances de l'Académie des Sciences. Serie C, Sciences chimiques 282 (3), 175-177.

Mabon G, Cariou M, Simonet J (1989) The cathodic coupling of heterocyclic activat-ed thioketones. A new and efficient route to π-donors (I)—the synthesis of polysubstituted bipyranylidenes from 4H-pyran 4-thiones. New journal of chemistry 13 (8-9), 601-607.

Negishi K, Aikawa K, Mikami K (2016) Cyclic-Protected Hexafluoroacetone as an Air-Stable Liquid Reagent for Trifluoromethylations. European Journal of Organic Chemistry 23, 4099-4104.

Reynolds G A, Chen C H (1980) Synthesis of unsymmetrical Δ$^{4,4}$-4-bi-4H-pyrans and thiopyrans. Journal of Organic Chemistry 45, 2458-2459.

Siegmund B, Mischok A, Benduhn J, Zeika O, Ullbrich S, Nehm F, Böhm M, Spoltore D, Fröb H, Körner C, Leo K, Vandewal K (2017) Organic narrowband near-infrared photodetectors based on intermolecular charge-transfer absorption. Nature Communications 8, 15421.

Strzelecka H, Schoenfelder W, Rivory J (1979) Electrical and optical properties of conducting TCNQ salts. Molecular Crystals and Liquid Crystals 52, 307-317.

The invention claimed is:
1. A compound according to formula (I)

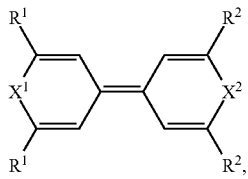

wherein
$X^1$ and $X^2$ are each independently selected from the group consisting of oxygen, sulfur and selenium,
$R^1$ and $R^2$ are each independently selected from the group consisting of substituted thiophene and selenophene residues.

2. The compound according to claim 1, wherein $R^1$ and $R^2$ are each independently selected from the group consisting of

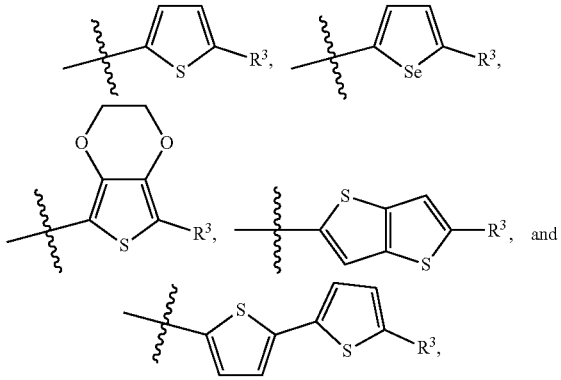

wherein $R^3$ is selected from C1 to C20 alkyl and cycloalkyl residues, C1 to C20 perfluoroalkyl residues, C1 to C20 aryl and heteroaryl residues, C1 to C20 alkoxy and thiaalkoxy residues, and primary, secondary and tertiary C1 to C20 alkylamino residues.

3. The compound according to claim 1, wherein $R^3$ is selected from the group including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclobutyl, cyclopentyl, cyclohexyl, cycloheptyl, trifluoromethyl, pentafluoroethyl, heptafluoropropyl, iso-pentafluoropropyl, nonafluorobutyl, tert-nonafluorobutyl, iso-nonafluorobutyl, 2,2,2-trifluoroethyl, 2,2,3,3,3-pentafluoropropyl, 2,2,3,3,4,4,4-heptafluorobutyl, 2,2,3,3,4,4,5,5-nonafluoropentyl, 2,2,3,4,4,5,5,6,6-unododecafluorohexyl, phenyl, benzyl, diphenyl, naphthyl, anthryl, phenanthryl, pyridyl, furanyl, thienyl, thiazyl, oxazyl, imidazyl, pyrimidyl, thiazinyl, methoxy, ethoxy, propoxy, butoxy, pentoxy, thiomethoxy, thioethoxy, thiopropoxy, iso-thiopropoxy, thiobutoxy, iso-thiobutoxy, tert-thiobutoxy, thiohexoxy, iso-thiohexoxy, amino, methylamino, butylamino, tolylamino, dimethylamino, diethylamino, methylphenylamino, methyltolylamino, pyrrolidine, piperidine, morpholine, thiomorpholine and ditolylamine.

4. The compound according to claim 1, wherein $R^1$ and $R^2$ are identical.

5. The compound according to claim 1, wherein $X_1$ and $X^2$ are each independently selected from the group consisting of sulfur and selenium.

6. The compound according to claim 1, wherein $X_1$ and $X^2$ are identical.

7. The compound according to claim 1, wherein $X_1$ and $X^2$ are oxygen and sulfur, oxygen and selenium, or sulfur and selenium.

8. An electronic or optoelectronic component comprising the compound according to claim 1.

9. The electronic or optoelectronic component according to claim 8, wherein said electronic or optoelectronic component is selected from:
an organic solar cell (OSC) donor absorber material;
a hole transport material (HTM) in dye-sensitized solar cells (DSSC, Gratzel cells);
a organic integrated circuit (O-IC);
an organic field-effect transistor (OFET);
an organic thin-film transistor (O-TFT);
an organic light emitting diode (OLED);
a photodetector; and
an IR sensor.

10. The electronic or optoelectronic component according to claim 8, wherein said electronic or optoelectronic component is an infrared (IR) charge transfer (CT) absorption sensor.

11. The compound according to claim 2, wherein $R^3$ is selected from the group including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclobutyl, cyclopentyl, cyclohexyl, cycloheptyl, trifluoromethyl, pentafluoroethyl, heptafluoropropyl, iso-pentafluoropropyl, nonafluorobutyl, tert-nonafluorobutyl, iso-nonafluorobutyl, 2,2,2-trifluoroethyl, 2,2,3,3,3-pentafluoropropyl, 2,2,3,3,4,4,4-heptafluorobutyl, 2,2,3,3,4,4,5,5-nonafluoropentyl, 2,2,3,4,4,5,5,6,6-unododecafluorohexyl, phenyl, benzyl, diphenyl, naphthyl, anthryl, phenanthryl, pyridyl, furanyl, thienyl, thiazyl, oxazyl, imidazyl, pyrimidyl, thiazinyl, methoxy, ethoxy, propoxy, butoxy, pentoxy, thiomethoxy, thioethoxy, thiopropoxy, iso-thiopropoxy, thiobutoxy, iso-thiobutoxy, tert-thiobutoxy, thiohexoxy, iso-thiohexoxy, amino, methylamino, butylamino, tolylamino, dimethylamino, diethylamino, methylphenylamino, methyltolylamino, pyrrolidine, piperidine, morpholine, thiomorpholine and ditolylamine.

12. The compound according to claim 2, wherein $R^1$ and $R^2$ are identical.

13. The compound according to claim 3, wherein $R^1$ and $R^2$ are identical.

14. The compound according to claim 2, wherein $X^1$ and $X^2$ are each independently selected from the group consisting of sulfur and selenium.

15. The compound according to claim 3, wherein $X^1$ and $X^2$ are each independently selected from the group consisting of sulfur and selenium.

16. The compound according to claim 2, wherein $X^1$ and $X^2$ are identical.

17. The compound according to claim 3, wherein $X^1$ and $X^2$ are identical.

18. The compound according to claim 2, wherein $X^1$ and $X^2$ are oxygen and sulfur, oxygen and selenium, or sulfur and selenium.

19. The compound according to claim 3, wherein $X^1$ and $X^2$ are oxygen and sulfur, oxygen and selenium, or sulfur and selenium.

20. The compound according to claim 11, wherein $R^1$ and $R^2$ are identical, and
$X^1$ and $X^2$ are identical and are selected from the group consisting of sulfur and selenium; or $X^1$ and $X^2$ are oxygen and sulfur, oxygen and selenium, or sulfur and selenium.

\* \* \* \* \*